US012654003B2

(12) United States Patent
Fraysse et al.

(10) Patent No.: US 12,654,003 B2
(45) Date of Patent: Jun. 16, 2026

(54) ELECTRODE PLACEMENT APPARATUS AND METHODS

(71) Applicant: Medtronic, Inc., Minneapolis, MN (US)

(72) Inventors: Estelle Fraysse, Eindhoven (NL); Maurice Verbeek, Geleen (NL)

(73) Assignee: Medtronic, Inc., Minneapolis, MN (US)

( * ) Notice: Subject to any disclaimer, the term of this patent is extended or adjusted under 35 U.S.C. 154(b) by 1323 days.

(21) Appl. No.: 17/379,440

(22) Filed: Jul. 19, 2021

(65) Prior Publication Data

US 2022/0032047 A1 Feb. 3, 2022

Related U.S. Application Data

(60) Provisional application No. 63/058,812, filed on Jul. 30, 2020.

(51) Int. Cl.
| | |
|---|---|
| *A61N 1/05* | (2006.01) |
| *A61M 25/00* | (2006.01) |
| *A61M 25/01* | (2006.01) |
| *A61M 25/02* | (2006.01) |
| *A61M 25/04* | (2006.01) |
| *A61N 1/362* | (2006.01) |
| *A61N 1/37* | (2006.01) |

(52) U.S. Cl.
CPC ....... *A61N 1/0573* (2013.01); *A61M 25/0082* (2013.01); *A61M 25/0105* (2013.01); *A61M 25/04* (2013.01); *A61N 1/3622* (2013.01); *A61N 1/3702* (2013.01); *A61M 2025/0286* (2013.01); *A61M 2210/125* (2013.01); *A61N 2001/058* (2013.01)

(58) Field of Classification Search
CPC .. A61N 1/0573; A61N 1/3622; A61N 1/3702; A61N 2001/058; A61N 1/3627; A61N 1/057; A61N 1/05; A61M 25/0082; A61M 25/0105; A61M 25/04; A61M 2025/0286; A61M 2210/125
See application file for complete search history.

(56) References Cited

U.S. PATENT DOCUMENTS

| | | | |
|---|---|---|---|
| 3,814,104 A | 6/1974 | Irnich et al. | |
| 3,943,936 A | 3/1976 | Rasor et al. | |
| (Continued) | | | |

FOREIGN PATENT DOCUMENTS

| | | |
|---|---|---|
| EP | 1428550 | 6/2004 |
| WO | 2002/022202 | 3/2002 |
| WO | 2006/118865 | 11/2006 |

OTHER PUBLICATIONS

Haqqani et al., "The Implantable Cardioverter-Defibrillator Lead: Principles, Progress and Promises," PACE, vol. 32, pp. 1336-1353, Oct. 2009.

(Continued)

*Primary Examiner* — Niketa Patel
*Assistant Examiner* — Adreanne A. Arnold
(74) *Attorney, Agent, or Firm* — Mueting Raasch Group

(57) ABSTRACT

Apparatus and methods for placement of electrodes into selected tissue, such as the septal wall separating the left and right ventricles, with, in some cases, access to the septal wall from the right ventricle. Torque sleeves may be used to provide for rotation as needed.

20 Claims, 7 Drawing Sheets

(56) References Cited

U.S. PATENT DOCUMENTS

| | | | |
|---|---|---|---|
| 4,103,690 | A | 8/1978 | Harris |
| 4,142,530 | A | 3/1979 | Wittkampf |
| 4,269,198 | A | 5/1981 | Stokes |
| 4,280,512 | A | 7/1981 | Karr et al. |
| 4,858,623 | A | 8/1989 | Bradshaw et al. |
| 4,936,823 | A | 6/1990 | Colvin et al. |
| 5,193,540 | A | 3/1993 | Schulman et al. |
| 5,246,014 | A | 9/1993 | Williams et al. |
| 5,411,535 | A | 5/1995 | Fujii et al. |
| 5,573,540 | A | 11/1996 | Yoon |
| 5,683,447 | A | 11/1997 | Bush et al. |
| 5,728,140 | A | 3/1998 | Salo et al. |
| 6,007,558 | A | 12/1999 | Ravenscroft et al. |
| 6,151,525 | A | 11/2000 | Soykan et al. |
| 6,240,322 | B1 | 5/2001 | Peterfeso et al. |
| 6,286,512 | B1 | 9/2001 | Loeb et al. |
| 6,409,674 | B1 | 6/2002 | Brockway et al. |
| 6,575,967 | B1 | 6/2003 | Leveen et al. |
| 6,783,499 | B2 | 8/2004 | Schwartz |
| 6,915,149 | B2 | 7/2005 | Ben-Haim |
| 6,944,507 | B2 | 9/2005 | Froeberg et al. |
| 6,978,178 | B2 | 12/2005 | Sommer et al. |
| 7,103,418 | B2 * | 9/2006 | Laske ................. A61N 1/0587 |
| | | | 604/506 |
| 7,290,743 | B2 | 11/2007 | Nowack |
| 7,321,798 | B2 | 1/2008 | Muhlenberg et al. |
| 7,418,298 | B2 | 8/2008 | Shiroff et al. |
| 8,353,940 | B2 | 1/2013 | Benderev |
| 9,579,501 | B2 | 2/2017 | Shuros et al. |
| 2002/0103424 | A1 | 8/2002 | Swoyer et al. |
| 2002/0165589 | A1 | 11/2002 | Imran et al. |
| 2003/0088301 | A1 | 5/2003 | King |
| 2004/0059348 | A1 * | 3/2004 | Geske ................... A61N 1/056 |
| | | | 606/129 |
| 2004/0147973 | A1 | 7/2004 | Hauser |
| 2004/0230281 | A1 | 11/2004 | Heil et al. |
| 2006/0084965 | A1 | 4/2006 | Young |
| 2006/0085039 | A1 | 4/2006 | Hastings et al. |
| 2006/0085041 | A1 | 4/2006 | Hastings et al. |
| 2008/0103572 | A1 | 5/2008 | Gerber |
| 2009/0082828 | A1 | 3/2009 | Ostroff |
| 2009/0259272 | A1 | 10/2009 | Reddy et al. |
| 2010/0069983 | A1 * | 3/2010 | Peacock, III .......... A61N 1/057 |
| | | | 607/9 |
| 2012/0172892 | A1 | 7/2012 | Grubac et al. |
| 2014/0039591 | A1 | 2/2014 | Drasler et al. |
| 2014/0067036 | A1 * | 3/2014 | Shuros ................. A61N 1/0573 |
| | | | 606/129 |
| 2015/0039070 | A1 | 2/2015 | Kuhn et al. |
| 2019/0111265 | A1 | 4/2019 | Zhou |
| 2019/0366081 | A1 * | 12/2019 | Kveen ................. A61N 1/0573 |
| 2020/0261734 | A1 | 8/2020 | Yang et al. |

OTHER PUBLICATIONS

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, pp. 1487-1498, Dec. 26, 2017.
Tjong et al., "The modular cardiac rhythm management system: the EMPOWER leadless pacemaker and the EMBLEM subcutaneous ICD," Herzschrittmachertherapie + Elektrophysiologie, vol. 29, pp. 355-361, Oct. 31, 2018.
International Search Report and Written Opinion from PCT Application PT/US2021/042485 dated Oct. 26, 2021, 15 pages.

* cited by examiner

Frontal plane
through heart

Sinoatrial
(SA) node
1

Anterior internodal
2

Atrioventricular
(AV) node
3

Middle
internodal
4

Posterior
internodal
5

Right atrium
26

Right ventricle
28

Arch of aorta
6

12

Left atrium
33

Atrioventricular (AV)
bundle (bundle of His)
13

Left ventricle
32

Left bundle
branches
8a

Right bundle
branches
8b

Anterior view of frontal section

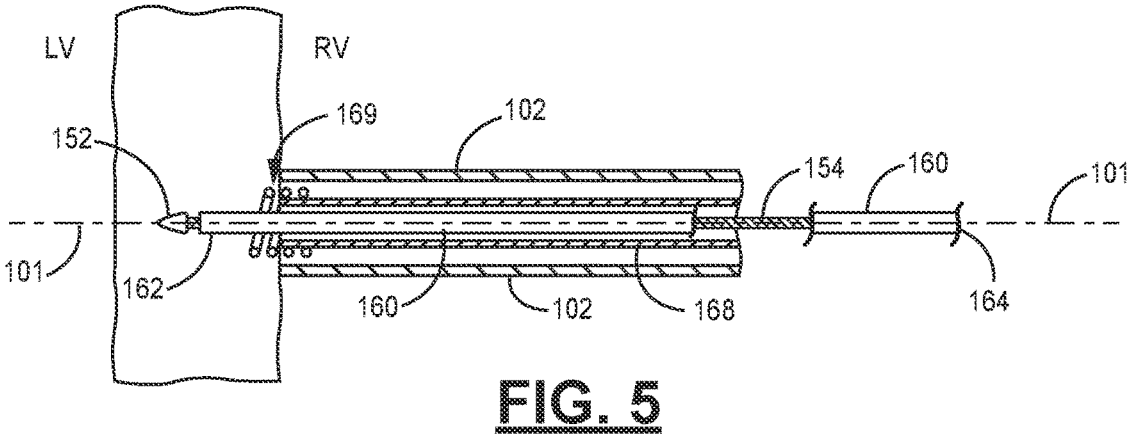
FIG. 5
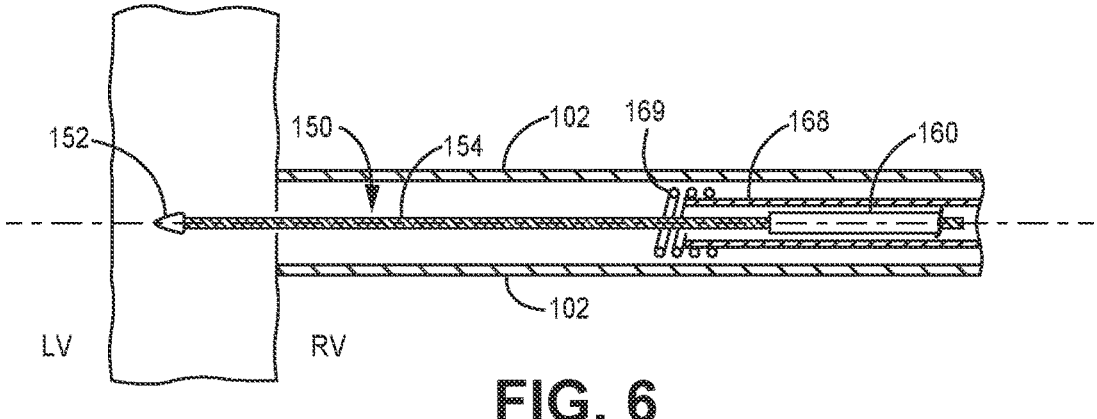
FIG. 6
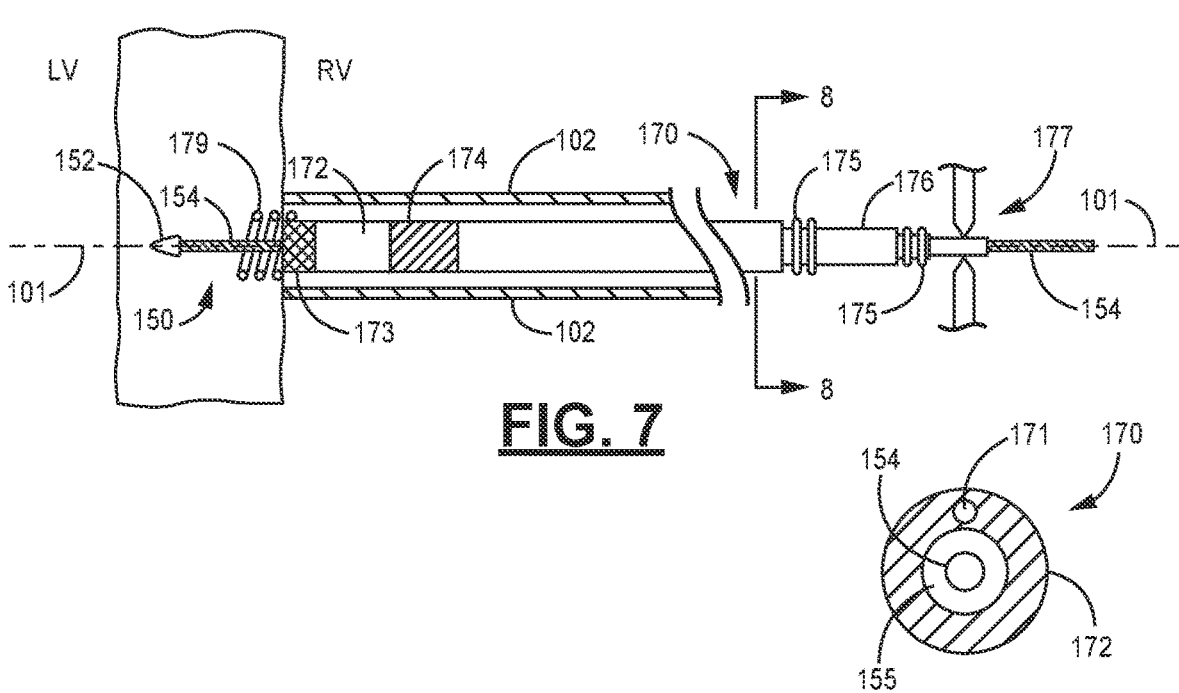
FIG. 7
FIG. 8

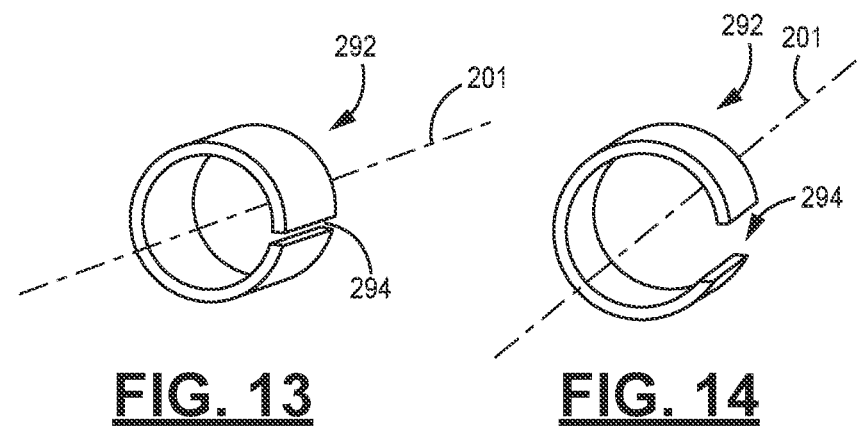
FIG. 13     FIG. 14
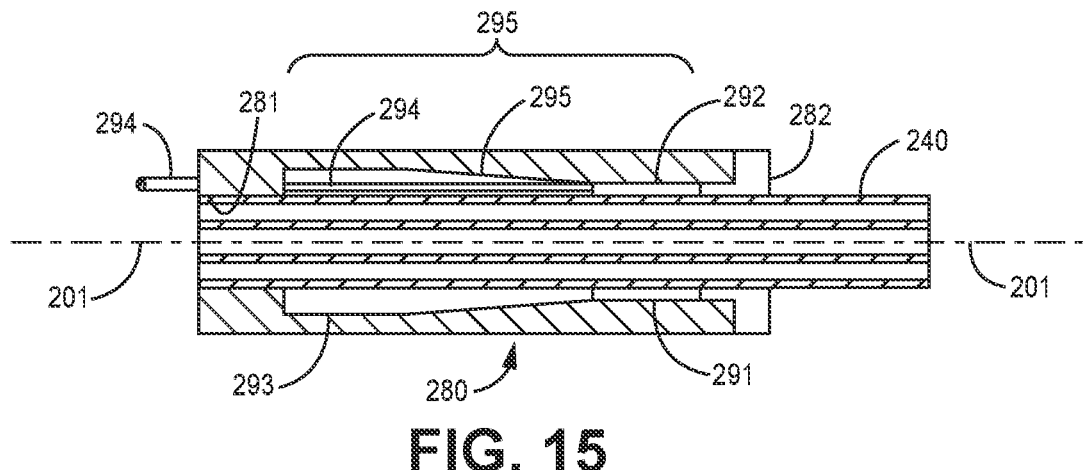
FIG. 15
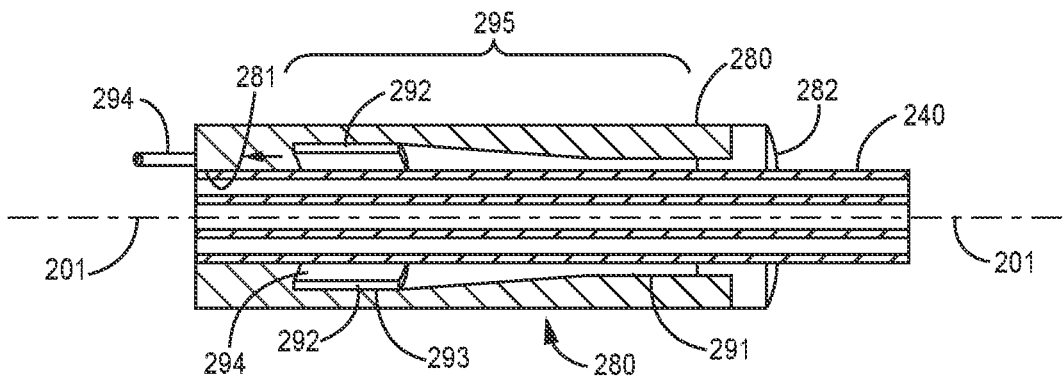
FIG. 16

ELECTRODE PLACEMENT APPARATUS AND METHODS

RELATED APPLICATION

This application claims the benefit under 35 U.S.C. § 119 of U.S. Provisional Application Ser. No. 63/058,812, filed 30 Jul. 2020, and titled ELECTRODE PLACEMENT APPARATUS AND METHODS, which is incorporated herein by reference in its entirety.

FIELD

The present disclosure relates generally to apparatus and methods used for placing electrodes at selected locations within tissue for, e.g., pacing and/or monitoring of cardiac or other tissue.

BACKGROUND

Implantable medical devices (IMDs), such as cardiac pacemakers or implantable cardioverter defibrillators, deliver therapeutic stimulation to patients' hearts thereby improving the lives of millions of patients living with heart conditions. Conventional pacing techniques involve pacing one or more of the four chambers of patient's heart 12—left atrium (LA) 33, right atrium (RA) 26, left ventricle (LV) 32 and right ventricle (RV) 28, all of which are shown in FIG. 1.

Over time, the left ventricle can become significantly inefficient at pumping blood to the body. In some patients, heart failure can develop such that the heart is too weak to pump blood to the body. Heart failure may be a devastating diagnosis since, for example, fifty percent of the heart failure patients have a life expectancy of five years. To avoid the potential development of heart failure, some physicians have considered alternative pacing methods that involve the cardiac conduction system. The cardiac conduction system, like a "super highway," may be described as quickly conducting electrical pulses whereas pacing cardiac muscle tissue may slowly conduct electrical pulses, like "traveling on a dirt road."

The cardiac conduction system includes sinoatrial node (SA node) 1, atrial internodal tracts 2, 4, 5 (i.e., anterior internodal 2, middle internodal 4, and posterior internodal 5), atrioventricular node (AV node) 3, His bundle 13 (also known as atrioventricular bundle or bundle of His), and right and left bundle branches 8a, 8b. FIG. 1 also shows the arch of aorta 6. The SA node, located at the junction of the superior vena cava and right atrium, is considered to be the natural pacemaker of the heart since it continuously and repeatedly emits electrical impulses. The electrical impulse spreads through the muscles of right atrium 26 to left atrium 33 to cause synchronous contraction of the atria. Electrical impulses are also carried through atrial internodal tracts to atrioventricular (AV) node 3—the sole connection between the atria and the ventricles. Conduction through the AV nodal tissue takes longer than through the atrial tissue, resulting in a delay between atrial contraction and the start of ventricular contraction. The AV delay, which is the delay between atrial contraction and ventricular contractor, allows the atria to empty blood into the ventricles. Then, the valves between the atria and ventricles close before causing ventricular contraction via branches of the bundle of His. The His bundle 13 is located in the membranous atrioventricular septum near the annulus of the tricuspid valve. The His bundle 13 splits into right and left bundle branches 8a, 8b.

SUMMARY

The techniques of this disclosure generally relate to apparatus and methods for placement of electrodes into selected tissue such as, e.g., the septal wall separating the left and right ventricles, with, in some cases, access to the septal wall from the right ventricle.

Although placement of electrodes in the septal wall from the right ventricle to, e.g., pace one or both of the bundle branches can be accomplished using conventional medical electrode leads, doing so may involve placing stresses on the leads that exceed their designed capacities. For example, use of leads having helical electrodes configured to be advanced through tissue by rotating the lead with its helical tip electrode may result in torque forces that exceed recommended limits for the medical leads. To address that issue, the medical electrode kits, catheter assemblies, and/or methods described herein may include a torque sleeve capable of selectively clamping the medical leads to be rotated and being used to rotate the clamped medical leads so that the forces needed to rotate helical electrodes and/or fixation structures on the medical leads are carried by the torque sleeve rather than the medical lead itself.

In one or more embodiments, the torque sleeve may be removed after use or may be advanced to contact the surface of tissue (such as, e.g., a septal wall, etc.) in which in electrode of a medical lead is located and clamped on the medical lead to limit or prevent migration of the implanted portion of the medical lead further into the tissue (where, for example, the medical lead could extend out of the opposite side of a septal wall, etc.).

In other embodiments, at least one lead of a medical electrode kit and/or catheter assembly described herein may be advanced into tissue through linear or translational motion to avoid the need for rotation and the stresses associated therewith.

In a first aspect, one or more embodiments of a medical electrode kit as described herein may include: a delivery catheter extending along a catheter axis from a proximal catheter end to a distal catheter end, the delivery catheter comprising a delivery lumen extending from a distal opening at the distal catheter end towards the proximal catheter end; a catheter fixation structure located at the distal catheter end, the catheter fixation structure configured to attach the distal catheter end to tissue; a first lead assembly located in the delivery catheter lumen. The first lead assembly may include: a push tube comprising a tube lumen extending from a distal tube opening proximally towards a proximal tube end, the push tube located within the delivery lumen extending along the catheter axis, and a first lead comprising a first electrode positioned at the distal tube opening and a first conductor attached to the first electrode, the first conductor extending proximally away from the first electrode and towards the proximal tube end. The medical electrode kit may further include a second lead extending from a distal end to a proximal end along a second lead axis, the second lead comprising: a second lead body comprising a first lead lumen extending from a lead opening at the distal end of the second lead proximally towards the proximal end of the second lead, a lead fixation structure located at the distal end of the second lead, the lead fixation structure configured to attach the distal end of the second lead to tissue, and a second electrode exposed on an exterior surface of the second lead body, the second electrode located between the distal end of the second lead and the proximal end of the second lead, wherein the second electrode is configured to be spaced away from tissue to which the lead fixation structure is attached; wherein the second lead is configured for advancement over the first conductor of the first lead distally towards the first electrode after the push tube and the delivery catheter are both removed from the first conductor in a proximal direction, and wherein the first conductor is located in the first lead lumen when the second lead is advanced over the first conductor towards the first electrode.

In a second aspect, one or more embodiments of a medical therapy system as described herein may include: an implantable medical device (IMD) configured to provide pacing of a patient's heart; and a medical electrode kit as described herein, wherein the first lead and the second lead of the medical electrode kit are configured to be connected to the IMD.

In a third aspect, one or more embodiments of an implanted medical therapy system as described herein may include an implantable medical device (IMD) configured to provide pacing of a patient's heart, wherein the IMD is subcutaneously implanted in the patient; with the first lead and the second lead of a medical electrode kit as described herein are implanted in the patient and connected to the IMD.

In a fourth aspect, one or more embodiments of a method of implanting a medical electrode system as described herein may include: advancing a distal catheter end of a delivery catheter into a right ventricle of a patient's heart; securing a catheter fixation structure at the distal catheter end of the delivery catheter at a selected location on the septal wall of the patient's heart after advancing the distal catheter end into the right ventricle; advancing a first lead assembly through a delivery lumen in the delivery catheter, wherein the first lead assembly comprises a push tube and a first lead comprising a first electrode and first conductor attached to the first electrode, wherein advancing the first lead assembly comprises pushing the first electrode out of the distal catheter end of the delivery catheter and into the septal wall to locate the first electrode in the septal wall, wherein the first conductor extends proximally from the first electrode into the delivery lumen of the delivery catheter after the first electrode is located in septal wall; removing the push tube from the first conductor of the first lead after the first electrode is located in septal wall; removing the catheter fixation structure of the delivery catheter from the septal wall after the first electrode is located in septal wall; removing the delivery catheter from the first conductor of the first lead after removing the catheter fixation structure of the delivery catheter from the septal wall; advancing a second lead over the first conductor of the first lead after removing the delivery catheter from the first conductor of the first lead, wherein at least a portion of the first conductor is located in a first lead lumen in a second lead body while advancing the second lead over the first conductor; and securing the second lead body to the septal wall by attaching a lead fixation structure at a distal end of the second lead to the septal wall after advancing a second lead over the first conductor of the first lead, wherein the second lead comprises a second electrode located in the right ventricle when the lead fixation structure of the second lead is attached to the septal wall.

In a fifth aspect, one or more embodiments of a catheter assembly as described herein may include: a therapy lead extending along a catheter axis from a proximal lead end to a distal lead end, the therapy lead comprising one or more electrodes proximate the distal lead end; a therapy lead fixation structure located at the distal lead end of the therapy lead, the catheter fixation structure configured to attach the distal lead end to tissue; a torque sleeve comprising a sleeve lumen extending along a sleeve axis extending from a distal sleeve end to a proximal sleeve end, wherein the therapy lead is located in the sleeve lumen of the torque sleeve; and a clamp assembly located in a clamping section of the sleeve lumen proximate the distal sleeve end, wherein the clamp assembly is configured to frictionally couple the torque sleeve to the therapy lead when in a clamped state such that rotation of the torque sleeve about the catheter axis causes corresponding rotation of the therapy lead, and wherein the clamp assembly is configured to decouple the torque sleeve from the therapy lead when the clamp assembly is in an unclamped state such that the torque sleeve is configured to be advanced over the therapy lead towards the distal lead end.

In a sixth aspect, one or more embodiments of a method of implanting a therapy lead may include: advancing a distal lead end of a therapy lead to a selected location in a patient's heart, wherein the therapy lead extends along a catheter axis from a proximal lead end to a distal lead end, the therapy lead comprising one or more electrodes proximate the distal lead end, and wherein a portion of the therapy lead is located in a torque sleeve comprising a sleeve lumen extending along a sleeve axis extending from a distal sleeve end to a proximal sleeve end, wherein the distal sleeve end is located proximate the distal lead end; securing a lead fixation structure at the distal lead end of the therapy lead to tissue at a selected location in the patient's heart after advancing the distal lead end to the selected location, wherein the securing comprises rotating the therapy lead about the catheter axis using the torque sleeve while a clamp assembly located in a clamping section of the sleeve lumen proximate the distal sleeve end is in a clamped state in which the clamp assembly frictionally couples the torque sleeve to the therapy lead such that rotation of the torque sleeve about the catheter axis causes corresponding rotation of the therapy lead; decoupling the torque sleeve from the therapy lead after securing the lead fixation structure to tissue at the selected location in the patient's heart by moving the clamp assembly to an unclamped state in which the torque sleeve is able to move along the therapy lead; advancing the distal sleeve end over the therapy lead towards the distal lead end after decoupling the torque sleeve from the therapy lead until the distal sleeve end contacts tissue surrounding the selected location; and moving the clamp assembly back to the clamped state in which the clamp assembly frictionally couples the torque sleeve to the therapy lead such that movement of the torque sleeve along the therapy lead is prevented.

BRIEF DESCRIPTION OF THE DRAWING

FIG. 5 depicts the lead and delivery catheter of FIG. 3 after advancement of the electrode and distal end of the push tube of the first lead assembly into the septal wall past the distal end of the delivery catheter.

FIG. 6 depicts the electrode of the first lead assembly inside a guide catheter in place in the septal wall after retraction of the push tube into the delivery catheter and after detachment of the delivery catheter from the septal wall.

FIG. 7 depicts the electrode of the first lead in place in the septal wall and a second lead attached to the septal wall after advancement of the second lead over the conductor of the first lead, with the first lead and the second lead located within a guide catheter.

FIG. 8 is a cross-sectional view of first lead and second lead of FIG. 7 taken along line 8-8 in FIG. 7.

FIG. 13 depicts one illustrative embodiment of a ring in a compressed state that may be used in one or more embodiments of a clamping catheter as described herein.

FIG. 14 depicts the ring of FIG. 12 in an expanded state.

FIG. 15 is a schematic diagram illustrating use of the ring of FIGS. 13-14 in one illustrative embodiment of a clamping catheter as described herein in which the ring is in the compressed state such that the clamping catheter is engaged with the illustrative embodiment of a medical lead located in the delivery lumen of the clamping catheter.

FIG. 16 depicts the clamping catheter and medical lead of FIG. 15 after disengagement of the ring from the medical lead to allow movement of the clamping catheter and medical lead relative to each other.

DETAILED DESCRIPTION

Figure 1:
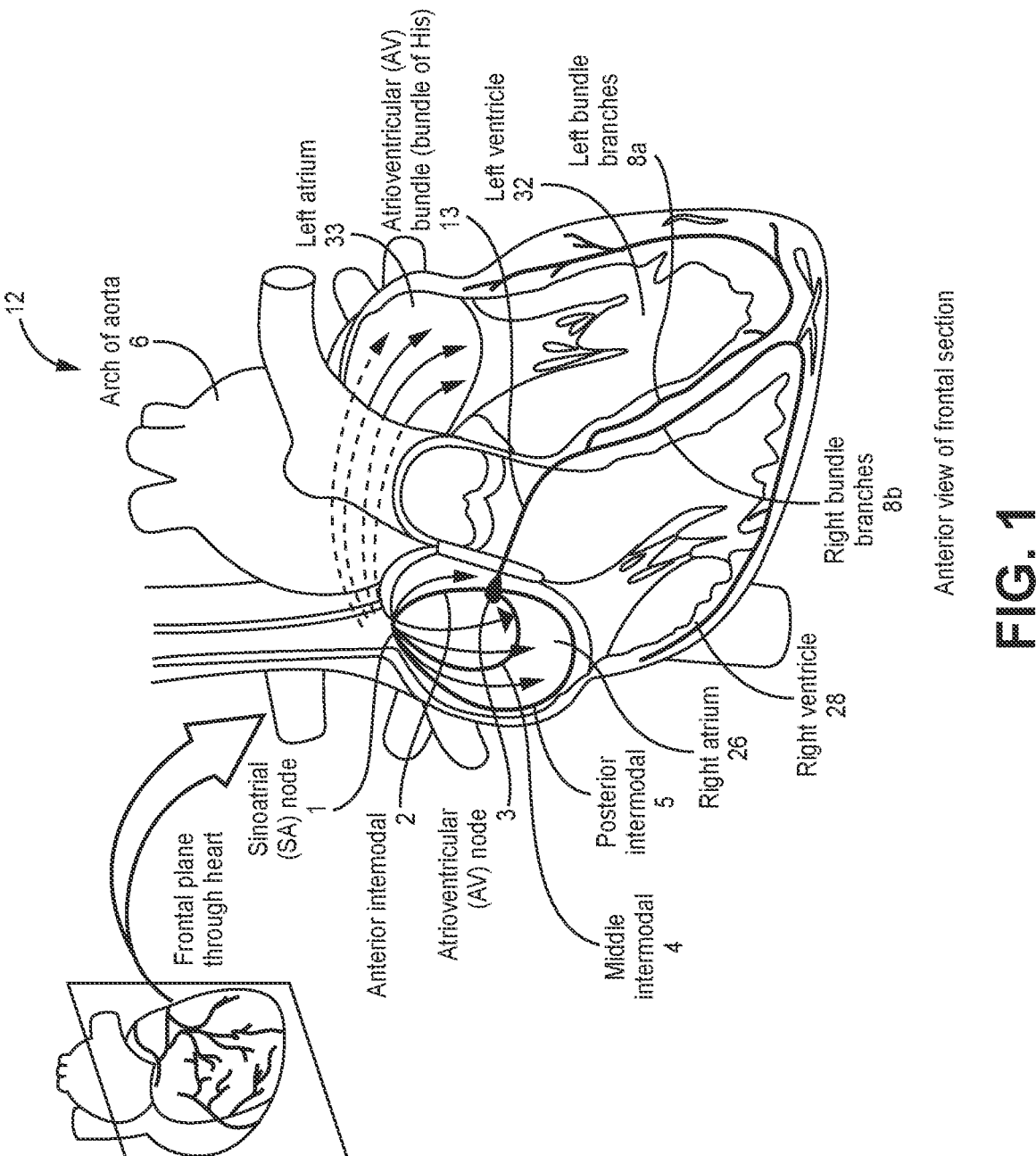
FIG. 1 is a schematic diagram of a heart of patient (prior art).

FIG. 1 shows patient's heart 12 along with an Implantable Medical Device (IMD) 16 operably coupled to implantable medical electrical lead 23 to deliver bundle branch pacing according to one example of an IMD system 10 as described herein. FIG. 1B is a close-up view of lead 23 in the patient's heart 12 of FIG. 1A. Although only one electrical lead is depicted in connection with the IMD system 10, one or more alternative embodiments of IMD systems using electrical leads as described herein may include two or more electrical leads implanted at various locations to monitor and/or provide therapy to a patient's heart 12.

Figures 2A, 2B:
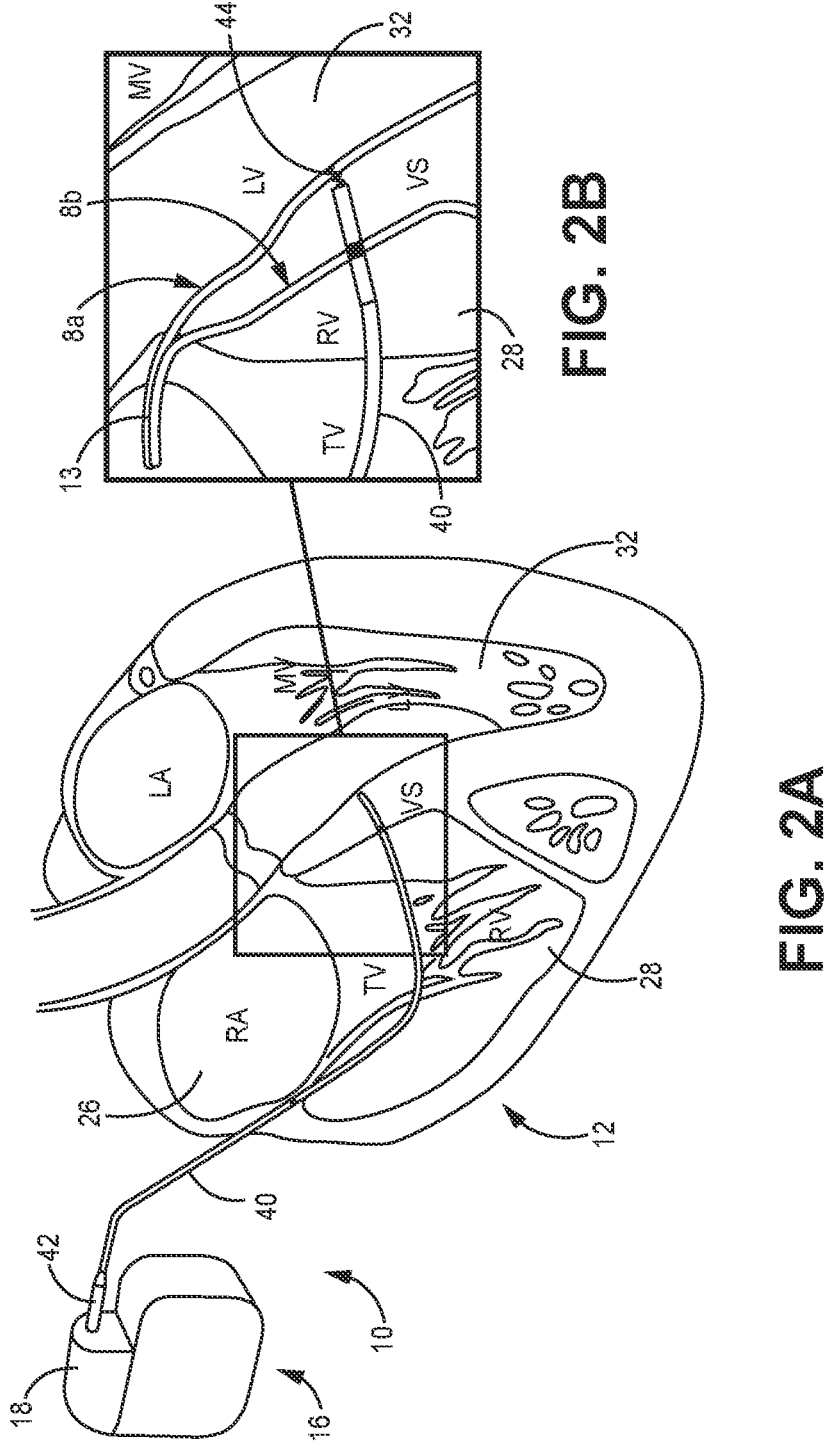
FIG. 2A is a conceptual diagram illustrating one illustrative embodiment of a therapy system (e.g., an implantable medical device) configured to provide therapy to a heart of patient through a lead placed either in the right ventricle using an implantable medical device (IMD).
FIG. 2B is a close-up view of the lead in the patient's heart of FIG. 2A.

FIGS. 2A-2B illustrate only one illustrative embodiment of a medical therapy system 10 that may be used to provide therapy to heart 12 of a patient. Patient ordinarily, but not necessarily, will be a human. Therapy system 10 includes IMD 16 which is coupled to at least one electrical lead 40. IMD 16 may be, for example, an implantable pacemaker, cardioverter, and/or defibrillator that provides electrical signals to heart 12 via electrodes coupled to electrical lead 40. Further non-limiting examples of IMD 16 include: a subcutaneous ICD (S-ICD), and a subcutaneous medical device (e.g., nerve stimulator, inserted monitoring device, etc.).

In one or more embodiments, IMD 16 is configured to provide cardiac stimulation therapy (e.g., defibrillation, cardioversion, and/or pacing), and may include a hermetically sealed housing in which the appropriate electronics and a power supply are contained. The housing may be formed from a conductive material, such as titanium, or from a combination of conductive and non-conductive materials. IMD 16 may include a connector module 18 by which the proximal ends of one or more leads 40 are electrically coupled to the electronics contained therein, for example, by electrical contacts contained within the module and a corresponding hermetically sealed feedthrough assembly, such as is known in the art. The conductive material of the device housing may be employed as an electrode, for example, to provide the aforementioned therapy in conjunction with pacing electrodes and/or a defibrillation electrodes on one or more leads 40. The distal ends of the one or more leads 40 connected to the IMD 16 may be implanted extrathoracically (e.g., within the subcutaneous tissue and/or muscle), transvenously, epicardially, pericardially or in other locations within a patient.

Depicted lead 40 extends into heart 12 to sense electrical activity of heart 12 and/or deliver electrical stimulation to heart 12 with the distal end 44 of the lead 40 located proximate the right bundle branch 44. In one or more embodiments, lead 40 is a bundle branch pacing lead. As used herein, the term "bundle branch pacing" refers to pacing the left bundle branch 8a, the right bundle branch 8b, and/or the His bundle 13 of the patient's heart 12. In the example shown in FIG. 2A, bundle pacing lead 40 extends through one or more veins and the vena cava, and into the right ventricle 28 of heart 12 to pace one or both of the left bundle branch 8a and the right bundle branch 8b. In some embodiments, one or more electrodes on the lead 40 may be positioned within about 1 millimeter of one or both bundle branches 8a and 8b.

Although only one electrical lead 40 is included in the depicted illustrative embodiment of therapy system 10 depicted in FIGS. 2A-2B, one or more alternate embodiments of therapy systems 10 described herein may include two or more additional electrical leads. For example, in one or more embodiments, a Right Ventricular (RV) lead (not shown) may extend through one or more veins, the superior vena cava, and right atrium (RA), and into right ventricle 28. In one or more embodiments, a Left Ventricular (LV) coronary sinus lead may extend through one or more veins, the vena cava, right atrium, and into the coronary sinus to a region adjacent to the free wall of left ventricle 32 of heart 12.

As illustrated in the embodiment depicted in FIGS. 2A-2B, lead 40 may be configured for single or dual bundle branch pacing, i.e., for pacing of both the right bundle branch and the left bundle branch. As illustrated, lead 40 is implanted in the septal wall from RV 28 toward LV 32. In one or more embodiments, lead 40 may not pierce through the septal wall or extend into the LV chamber 32.

Each of the one or more leads 40 may include an elongated, insulative lead body, which may carry any number of conductors separated from one another by tubular, insulative sheaths. The conductors are connected to electrodes on the one or more leads 40, with the electrodes being fabricated from any suitable electrically conductive material, such as, but not limited to, platinum, platinum alloy or other materials known to be usable in implantable electrodes.

Figure 3:
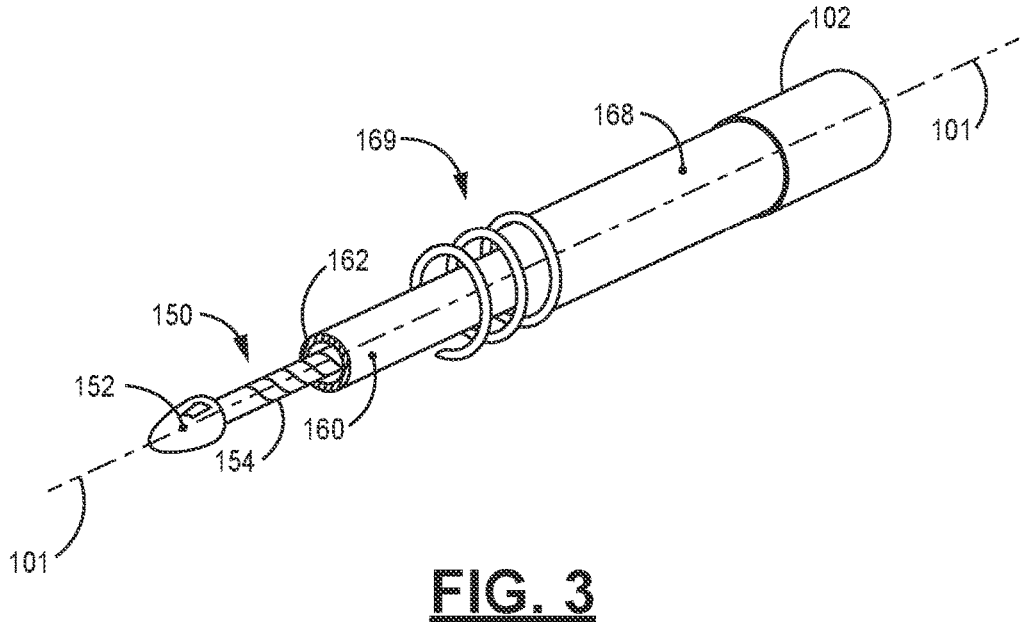
FIG. 3 is an enlarged view of one illustrative embodiment of a first lead assembly and delivery catheter as described herein protruding from the distal end of one illustrative embodiment of a guide catheter, with the distal end of the push tube of the first lead assembly advanced past the distal end of the delivery catheter and the electrode at the distal end of the conductor advanced out of the distal end of the push tube.

The components of one illustrative embodiment of a medical electrode kit configured for bundle branch pacing in a patient's heart is depicted in connection with FIGS. 3-8. As described herein, such a medical electrode kit may be provided in a package for use by a practitioner during a single procedure. With reference to FIG. 3, the distal portion of a first lead assembly including a first lead 150 and a push tube 160 are depicted as being extended out of a delivery catheter 168.

In FIGS. 4-7, various components of the medical electrode kit, i.e., the first lead 150, push tube 160, delivery catheter 168 and second lead 170, are all depicted as being delivered through a guide catheter 102 that is advanced to the attachment location. As described herein, the delivery catheter 168 and second lead 170 are rotated about the catheter axis 101 to implant the fixation structures 169 and 179 (respectively) located at the distal ends of the delivery catheter 168 and second lead 170. The guide catheter 102 prevents unwanted movement of the delivery catheter 168 and second lead 170 as they are rotated into and/or out of tissue as described herein. Upon implantation of the second lead 170 in tissue as depicted in FIG. 7, the guide catheter 102 will typically be withdrawn and/or split and withdrawn in the proximal direction and removed from the patient's heart. Examples of some potentially suitable guide catheters may include, but are not limited to, the guide catheters marketed by Medtronic, Inc. under the tradenames C315, C304, 6227DEF, etc.

The delivery catheter 168 extends along a catheter axis 101 that extends from a proximal end to a distal end. A catheter fixation structure 169 is located at the distal end of the delivery catheter 168, with the catheter fixation structure 169 being configured to attach the distal end of the delivery catheter 168 to tissue. In the depicted illustrative embodiment, the catheter fixation structure 169 on the delivery catheter 168 is in the form of a helix configured to advance into tissue when the delivery catheter 168 is rotated about the catheter axis 101. In one or more embodiments, the helix of the catheter fixation structure 169 is in the form of a helically coiled wire. The wire used in this embodiment (as well as other helically coiled wires used for fixation described herein) can have any profile shape, e.g., round, rectangular, oval, etc.

The delivery catheter 168 includes a delivery lumen, with the first lead 150 and push tube 160 of the first lead assembly being depicted as extending out of that delivery catheter lumen in FIG. 3. The delivery catheter lumen in delivery catheter 168 extends from the distal opening (from which push tube 160 extends in FIG. 3) at the distal end of the delivery catheter 168 towards the proximal end of the delivery catheter (not shown).

The push tube 160 includes a tube lumen extending from a distal tube opening 162 at the distal end of the push tube 160 towards a proximal tube end 164 (see FIG. 5) of the push tube 160. As described above, the push tube 160 is located within the delivery lumen of the delivery catheter 168 that extends along the catheter axis 101.

The first lead 150 of the first lead assembly includes a first electrode 152 positioned at the distal tube opening 162 and a first conductor 152 extending proximally away from the first electrode 150 and towards the proximal tube and 164.

The first electrode 152 may be used as an anode or cathode depending on the monitoring and/or therapy being delivered using the first lead 150. The first electrode 152 is, in the depicted embodiment, configured for advancement into tissue upon the application of a translational pushing force delivered along the catheter axis 101 two the first lead 150 using the push tube 160. In one or more embodiments, the first electrode 152 is configured to resist removal from tissue (into which the first electrode 152 has been advanced) in a proximal direction along the first conductor 154.

The depicted illustrative embodiment of first electrode 152 is in the form of a tapered body having a base larger than a distal tip, with the first conductor 154 being attached to the base of the first electrode 152. The first electrode 152 may be provided in many other alternative shapes and/or include alternative structures to resist removal from tissue after having been pushed into the tissue. For example, the first electrode 152 may include one or more spines, barbs, hooks, etc. that resist removal of the first electrode 152 from tissue into which the first electrode 152 has been advanced as described herein.

Figure 4:
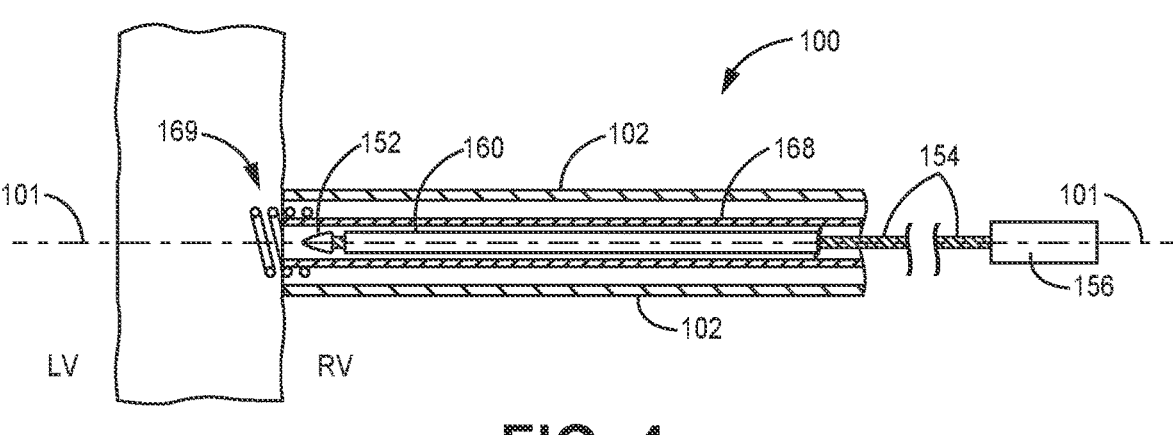
FIG. 4 schematically depicts the illustrative embodiment of a first lead assembly of FIG. 3 located in a delivery catheter which is, in turn, located in a guide catheter, wherein the delivery catheter is attached to the septal wall while the distal end of the first lead assembly is located proximal from the distal end of the delivery catheter.

The first lead assembly including first lead 150 and push tube 160 are depicted as being located within the delivery catheter lumen formed within delivery catheter 168 in FIG. 4. Further, the delivery catheter 168 is depicted as being positioned within the right ventricle (RV) with the catheter fixation structure 169 at the distal end of the delivery catheter 168 being attached to the septal wall separating the right ventricle (RV) from the left ventricle (LV). Other features depicted in FIG. 4 include a connector 156 at the proximal end of the first conductor 154, the connector 156 being configured for connection to an implantable medical device such as IMD 16 as depicted in FIG. 2A.

Turning to FIG. 5, the first lead assembly 150 has been advanced through the delivery lumen in the delivery catheter 168. In the depicted illustrative embodiment, advancing the first lead assembly 150 through the delivery lumen in the delivery catheter 168 includes pushing the first electrode 152 out of the distal end of the delivery catheter 168 and into the septal wall separating the left and right ventricles to locate the first electrode 152 in the tissue forming the septal wall. The first conductor 154 attached to the first electrode 152 extends proximally from the first electrode 152 into the delivery lumen of the delivery catheter after the first electrode 152 is located in the tissue forming the septal wall.

With reference to FIG. 6, the first lead 150 is depicted as being attached to the septal wall after removal of the push tube 160, as well as removal of the delivery catheter 168 from the septal wall separating the left and right ventricles. Removing the push tube 160 involves withdrawing the push tube 160 in a proximal direction away from the first electrode 152 along the first conductor 154 because, as described herein, the first conductor 154 extends through a lumen formed in the push tube 160. In one or more alternative embodiments, the push tube 160 may include a slit or other splitting feature to facilitate splitting of the push tube 160 along the catheter axis 101 to facilitate its removal from the first conductor 154.

Removal of the catheter fixation structure 169 at the distal end of the delivery catheter 168 from the septal wall involves, in the depicted embodiment, rotation of the delivery catheter 168 about the catheter axis 101 to reverse the helix of catheter fixation structure 169 from the tissue forming the septal wall between the left and right ventricles. After the catheter fixation structure 169 has been removed or detached from the septal wall, the delivery catheter 168 is removed from the first conductor 154 of the first lead 150 by withdrawing the delivery catheter 168 in the proximal direction along catheter axis 101, with the first electrode 152 and first conductor 154 remaining attached to the septal wall separating the left and right ventricles. In one or more alternative embodiments, the delivery catheter 168 may include a slit or other splitting feature along at least a portion of its length to facilitate splitting of the delivery catheter 168 along the catheter axis 101 to facilitate its removal from the first conductor 154.

After both the push tube 160 and the delivery catheter 168 have been removed from the first conductor 154 of the first lead 150, a second lead 170 of the medical electrode kit may be advanced over the first conductor 154 of the first lead 150 towards the first electrode 152. In one or more embodiments, the second lead 170 may be described as extending from a distal end to a proximal end along the catheter axis 101 which, after removal of the delivery catheter 168 is defined by the first conductor 154.

Second lead 170 includes a second lead body 172 that includes a first lead lumen extending from a lead opening at the distal end of the second lead 170 proximally towards the proximal end of the second lead 170. With reference to the cross-sectional view of FIG. 8, at least a portion of the first conductor 154 is located within the first lead lumen 155 of the second lead body 172 while the second lead 170 is advanced over the first conductor 154 and, in one or more embodiments, at least a portion of the first conductor 154 is located within the first lead lumen 155 after the second lead 170 is in position such that the second lead 170 is attached to tissue as described herein.

Also seen in FIG. 8 is a conductor 171 extending along the lead body 172, with the conductor 171 being electrically connected to an electrode 174 provided on second lead 170. The conductor 171 extends in the proximal direction along catheter axis 101 within the second lead body 172 to a connector 176 located between seals 175 at the proximal end of the second catheter 170. The connector 176 and seals 175 are configured for connection to an implantable medical device such as, for example, IMD 16 depicted in FIG. 2A.

Second lead 170 also includes a lead fixation structure 179 located at the distal end of the second lead 170. The lead fixation structure 179 is configured to attach the distal end of the second lead 172 tissue such as, for example, the tissue forming the septal wall separating the left and right ventricles as seen in FIG. 7. In the depicted illustrative embodiment, the lead fixation structure 179 on the second lead 170 is in the form of a helix configured to advance into tissue when the second lead 170 is rotated about the first conductor 154 of the first lead 150 (which, in the depicted embodiment, corresponds with catheter axis 101). In one or more embodiments, the helix of the lead fixation structure 179 is in the form of a helically coiled wire. Attachment of the lead fixation structure 179 may be achieved by rotating the lead fixation structure 179 about the first conductor 154 of the first lead 150 such that the lead fixation structure 179 is embedded within the target tissue (e.g. the septal wall). In one or more embodiments, the lead fixation structure 179 may be configured to draw a portion of the lead body 172 into the tissue of the septal wall as the lead fixation structure 179 is rotated during advancement through tissue to its selected location.

In the depicted illustrative embodiment of second lead 170, an electrode 174 is exposed to an exterior surface of the second lead body 172. Electrode 174 may be a ring or cylindrical electrode located on the exterior of the lead body 172 proximal from the lead fixation structure 179. Electrode 174 may be used as an anode or cathode depending on the monitoring and/or therapy being delivered using the first lead 150 and second lead 170.

In one or more embodiments, the electrode 174 may be described as being located between the distal end of the second lead 170 (i.e., the end of the lead 170 at which the lead fixation structure 179 is located) and the proximal end of the second lead 170, with the electrode 174 being configured to be spaced away from tissue to which the lead fixation structure 179 is attached. In the depicted embodiment, the tissue to which the lead fixation structure 179 is attached is the septal wall separating the left and right ventricles of a heart. Because the second lead 170 approaches the septal wall from a location within the right ventricle, the electrode 174 on the exterior surface of the second lead body 172 is located within the right ventricle (RV) and is preferably not in contact with the tissue forming the septal wall.

Also depicted in connection with the illustrative embodiment of second lead 170 is a crimping process performed by a crimping device 170 that may be positioned to act on the proximal end of the second lead 170 near a location from which the first conductor 154 of the first lead 150 extends out of the second lead 170. Crimping or other attachment of the second lead 172 the first conductor 154 near the proximal ends of both the first lead 150 and the second lead 170 may be useful to prevent or limit migration of the first electrode 152 within tissue after attachment of the second lead 170 as described herein. Other techniques and/or structures configured to fix the position of the proximal end of the second lead 170 on the first conductor 154 of the first lead 150 may be used in place of crimping.

The depicted illustrative embodiment of second lead 170 also includes a monolithic controlled release device (MCRD) 173 at the distal end of the lead body 172. The MCRD 173 may be provided to deliver one or more substances such as, e.g., a steroid or other drug adjacent the location of the distal end of the second lead 170 when attached (e.g., the septal wall).

With the first lead 150 having its first electrode 152 located within the selected tissue (e.g., the septal wall that is depicted in FIG. 7) and the second lead 170 positioned over the first conductor 154 of the first electrode 150 and secured to the tissue in which the first electrode 152 of the first lead 150 is embedded, the electrodes 152 and 174 may be used to provide cardiac pacing and/or defibrillation, monitoring, or other electrical therapy to a patient.

Figure 9:
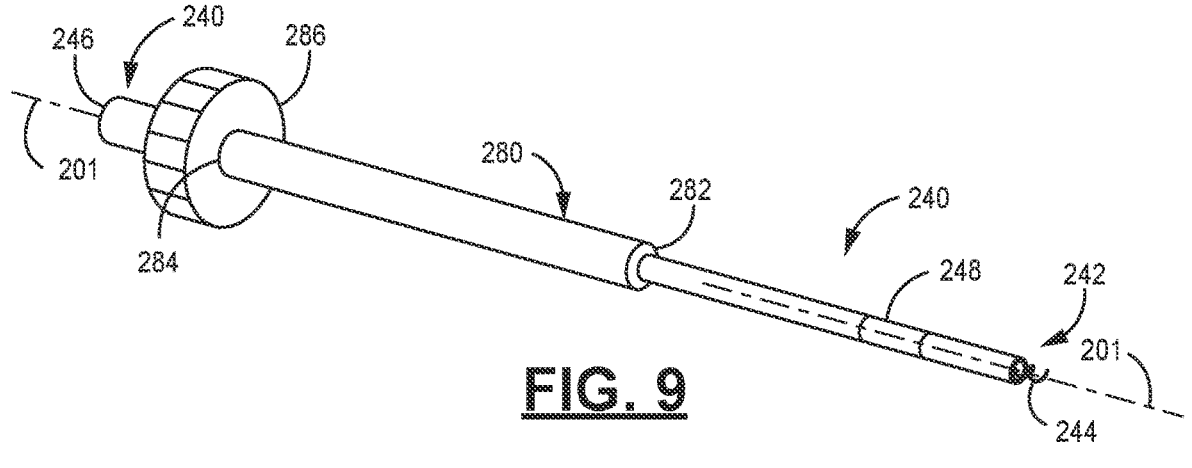
FIG. 9 is a perspective view of one illustrative embodiment of a distal portion of a medical lead extending out of the distal end of the delivery lumen of a clamping catheter.

With reference to FIGS. 9-16, catheter assemblies configured to deliver and/or retain therapy leads having one or more electrodes used to deliver therapy to a patient are described. The catheter assembly as depicted in FIG. 9 includes a therapy lead 240 and a torque sleeve 280. The torque sleeve 280 is, in one or more embodiments, provided to assist in rotating the therapy lead 240 about a catheter axis 201 and may, in one or more embodiments, also assist in retaining the therapy lead 240 in position after its attachment to a selected tissue. In particular, the torque sleeve 280 may reduce the stress on therapy lead 240 during rotation that could result in torque forces that exceed recommended limits for the therapy lead. Although not depicted in FIGS. 9-12, the catheter assembly will typically and preferably be delivered through a guide catheter as discussed above and depicted in FIGS. 3-7.

In one or more embodiments, the therapy lead 240 may be in the form of a second lead 170 provided as a component of a medical electrode kit as described herein (see, e.g., FIGS. 3-8). In other embodiments, the therapy lead 240 may be in the form of a bundle pacing lead such as, e.g., a SELECTSURE™ 3830 lead sold by Medtronic. A description of the SELECTSURE™ 3830 is found in the Medtronic model SELECTSURE™ 3830 manual (2013), incorporated herein by reference in its entirety. In yet another embodiment, the therapy lead 240 may be in the form of a bundle pacing lead such as is shown and described in U.S. Pat. No. 7,184,839 B2.

The therapy lead 240 depicted in FIG. 9 includes a pair of electrodes 244 and 248, with the electrode 244 in the form of a helical tip electrode and electrode 248 displaced proximally from the tip electrode 244 and being in the form of a cylindrical or ring electrode. The helical tip electrode is located at the distal end 242 of the therapy lead 240. The helical tip electrode 244 also functions as a catheter fixation structure that is configured to attach the distal end 242 of the catheter 242 tissue.

The torque sleeve 280 depicted in FIG. 9 includes a sleeve lumen extending along a sleeve axis which, in the depicted embodiment, is coextensive with the catheter axis 201. The sleeve lumen in torque sleeve 280 extends from a distal end 282 of the sleeve 282 a proximal end 284 of the sleeve 280.

The depicted embodiment of torque sleeve 280 also includes an optional rotation structure 286 attached to the torque sleeve 282 provide a location at which torque can be applied to the torque sleeve 280 when the catheter assembly including therapy lead 240 and torque sleeve 280 are used to implant the therapy lead 240 at a selected location.

The therapy lead 240 extends proximally from the proximal end 284 of the torque sleeve 280 as seen in FIG. 9 with the proximal end 246 of the therapy lead 240 being located proximally of the proximal end 284 of the torque sleeve 280 (although it should be understood that the proximal end 246 of the therapy lead 240 may or may not extend out of the proximal end 284 of the torque sleeve 280 in all instances.

Figure 10:
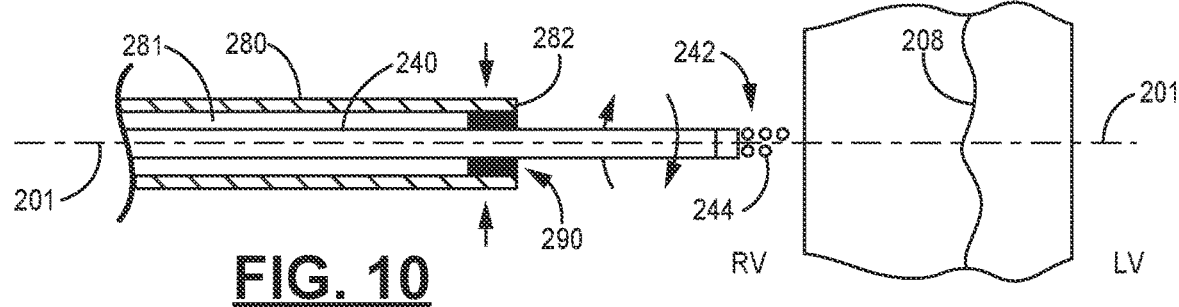
FIG. 10 is a schematic diagram illustrating one illustrative example of operation of a clamping catheter engaged with a medical lead located in a delivery lumen of the clamping catheter such that the clamping catheter can be used to rotate the medical lead to advance the medical lead into tissue.
Figure 11:
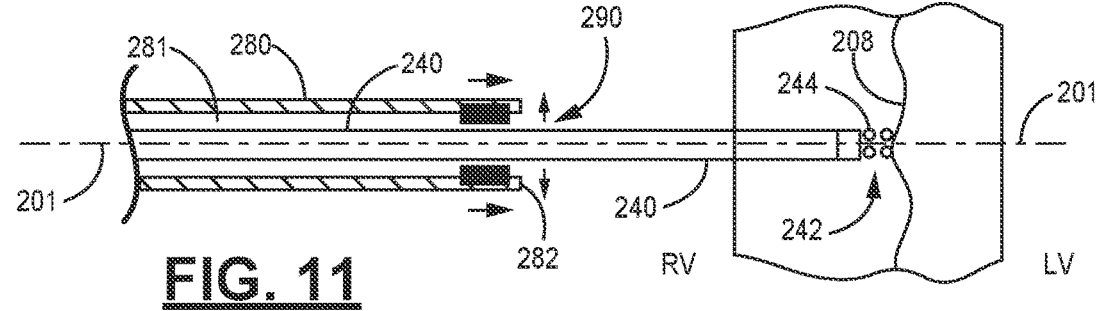
FIG. 11 depicts the clamping catheter and medical lead of FIG. 10 after the medical lead has been advanced into tissue and disengagement of the clamping catheter from the medical lead to allow for advancement of the clamping catheter over the lead towards the distal end of the medical lead.
Figure 12:
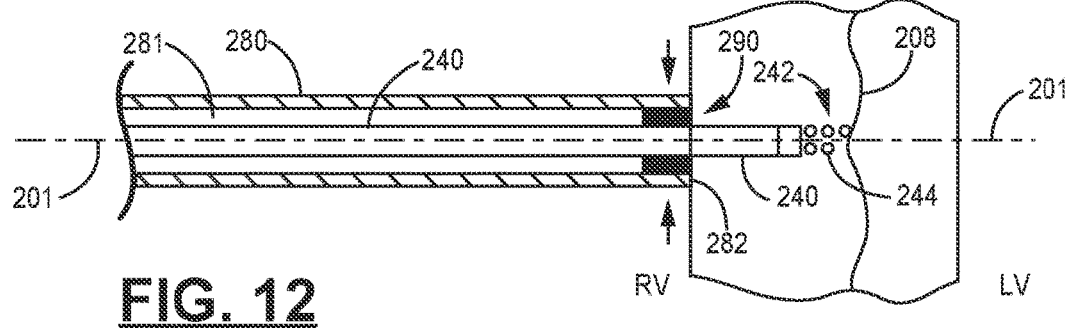
FIG. 12 depicts clamping catheter and medical lead of FIGS. 10-11 after advancement of the clamping catheter over the medical lead to the surface of the tissue in which the distal end of the medical lead is located and re-engagement of the clamping catheter on the medical lead to fix the position of the clamping catheter on the medical lead.

FIGS. 10-12 depict, schematically, use of the catheter assembly to attach the therapy lead 240 at a selected location in tissue. With reference to FIG. 10, the helical tip electrode 244 of the therapy lead 240 is shown approaching tissue which in the depicted embodiment, is in the form of a septal wall separating a right ventricle (RV) from a left ventricle (LV) in the heart of a patient (it being understood that the catheter assembly depicted in FIGS. 9-16 can be used in many other locations within the body of a patient). The septal wall depicted in FIG. 10 includes a bundle branch 208 located within the tissue of the septal wall.

Also depicted in FIG. 10 is the sleeve lumen 281 located within torque sleeve 280, with a portion of the therapy lead 240 located within that sleeve lumen 281. In the depicted embodiment, a portion of the therapy lead 240 extends past the distal end 282 of the torque sleeve 280 such that a portion of the therapy lead 240 is exposed outside of the sleeve lumen 281 of the torque sleeve 280.

In one or more embodiments of the catheter assemblies described herein, a clamp assembly 290 may be located in a clamping section of the sleeve lumen 281 proximate the distal end 282 of the sleeve. The clamp assembly 290 is configured to frictionally couple the torque sleeve 282 the therapy lead 240 when the clamp assembly is in a clamped state as seen in, e.g., FIG. 10. In the clamped state, rotation of the torque sleeve 280 about the catheter axis 201 causes corresponding rotation of the therapy lead 240 about the catheter axis 201. In one or more embodiments, the clamp assembly 290 may also prevent translational movement of the torque sleeve 280 along the length of the therapy lead 240 away from the distal end 242 of the therapy lead when the clamp assembly 290 is in the clamped state. In one or more embodiments, the clamp assembly 290 may prevent translational movement of the torque sleeve along the length of the therapy lead 240 towards the distal end 242 of the therapy lead 240 when the clamp assembly 290 is in the clamped state.

In one or more embodiments, the clamp assembly is configured to decouple the torque sleeve 280 from the therapy lead 240 when the clamp assembly 290 is in an unclamped state. When the clamp assembly is in the unclamped state, the torque sleeve 280 can be advanced over the therapy lead 240 towards the distal end 242 of the therapy lead 240.

The clamp assembly 290 is depicted in the clamped state in FIG. 10. Rotation of the torque sleeve 280, therefore, causes corresponding rotation of therapy lead 240 and, in particular, the fixation structure 244 located at the distal end 242 of the therapy lead 240. Rotation of that fixation structure 244 which, in one or more embodiments, is in the form of a helix configured to advance into tissue when rotated, causes the fixation structure 244 to advance into the tissue of the septal wall.

FIG. 11 depicts the catheter assembly of FIG. 10 after the clamp assembly 290 is moved to an unclamped state in which the clamp assembly 290 does not frictionally engage the therapy lead 240. The fixation structure 244 which, as described herein, may be in the form of a helical electrode, is embedded in the tissue of the septal wall and, in particular, is proximate the bundle branch 208 also depicted in the septal wall. When properly placed, the fixation structure/electrode 244 may be used to stimulate the bundle branch 208 and/or monitor electrical activity in the bundle branch 208.

FIG. 12 depicts the catheter assembly of FIG. 11 after the torque sleeve 280 has been advanced over the implanted therapy lead 240. That advancement occurs when the clamp assembly 290 is in an unclamped state as described herein. As depicted, however, in FIG. 12, the clamp assembly 290 has been moved back to its clamped state. As described herein, the clamp assembly 290 may prevent translational movement of the torque sleeve 280 along the therapy lead 240 away from the distal end 242 of the therapy lead 240 when the clamp assembly 290 is in the clamped state.

As depicted in FIG. 12, the torque sleeve 280 has been advanced over the implanted therapy lead 240 such that the distal end 282 of the torque sleeve 280 contacts the tissue into which the therapy lead 240 has been advanced. Contacting the tissue surrounding the entry location of the therapy lead 240 with the distal end 282 of the torque sleeve 280 may assist in securing the position of the therapy lead 240 in the tissue in which it is located by, for example, preventing further advancement of the therapy lead 240 through the tissue. Preventing further advancement of the therapy lead may, for example, prevent perforation of the septal wall on the left ventricular side of the septal wall due to unwanted further advancement of the therapy lead 240. Preventing further advancement of the therapy lead 240 using the torque sleeve 280 may also, for example, assist in retaining chosen positioning of the fixation structure/electrode 244 of therapy lead 240 within the tissue such that, for example, stimulation and/or monitoring of the bundle branch 208 is not interrupted.

Although the clamp assemblies used in one or more embodiments of torque sleeves of catheter assemblies as described herein may take a variety of forms, one illustrative embodiment of a clamp assembly is depicted in connection with FIGS. 13-18.

The depicted illustrative embodiment of a clamp assembly includes a split ring 292 located within a clamping section 295 of the sleeve lumen 281 of the torque sleeve 280 as seen in FIGS. 15-16. The illustrative embodiment of split ring 292 is depicted removed from the clamp assembly in FIGS. 13-14, with the catheter axis 201 provided for reference in both figures. The split ring 292 is shown in a compressed state in FIG. 13 and in an expanded state in FIG. 14. As seen in FIGS. 13-14, the gap 294 formed by the split ring 292 is narrower in the compressed state of FIG. 13 and wider in the expanded state of FIG. 14. In the compressed state of FIG. 13, the split ring 292 may be configured to contact and frictionally engage the outer surface of the therapy lead 240 as described herein. In the expanded state of FIG. 14, the split ring 292 may be large enough to allow the therapy lead 240 to pass through the split ring 292 without significant frictional engagement such that the split ring 292 can be advanced along the length of the therapy lead 240.

When unconstrained, the split ring 292 is in the expanded state as depicted in FIG. 14. The split ring 292 may be manufactured of any suitable material or combination of materials including one or more metals, one or more polymers, composites of two or more materials, etc. that provides the desired resiliency and friction when moved into contact with the therapy lead 240 as described herein.

The clamping section 295 of the sleeve lumen 281 has a tapered diameter that increases when moving in the proximal direction away from the distal end 282 of the torque sleeve 280 (and conversely, the diameter of the clamping section 295 decreases when moving in the distal direction toward the distal end 282 of the torque sleeve 280).

The split ring 292 is configured to clamp the exterior surface of the therapy lead 240 passing through the clamping section 295 of the sleeve lumen 281 such that the split ring 292 frictionally couples the torque sleeve 280 to the therapy lead 240 when the split ring 292 is located at the distal end 291 of the clamping section 295. This configuration is depicted in FIG. 15 and corresponds to the clamped state of the clamp assembly.

Figure 17:
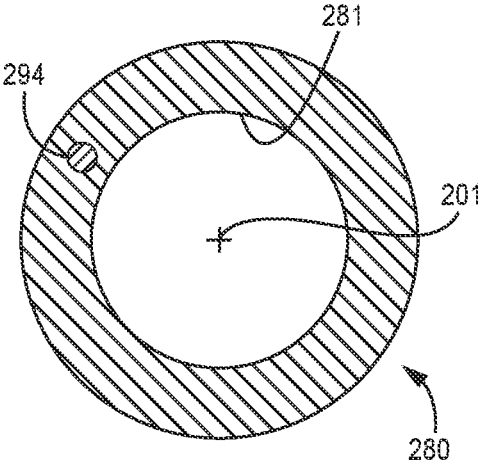
FIG. 17 is an enlarged cross-sectional view of the torque sleeve depicted in FIGS. 15-16 taken in a plane transverse to the catheter axis 201 at a location proximal the clamping section.

The depicted illustrative embodiment of the clamp assembly includes a clamp actuator 294 attached to the split ring 292. The clamp actuator 294 extends proximately through the torque sleeve 280 away from the split ring 292 and towards the proximal end of the sleeve 280. The torque sleeve 280 and clamp actuator 294 are depicted in an enlarged cross-sectional view in FIG. 17, with the cross-sectional view being taken in a plane transverse to the catheter axis 201. Sleeve lumen 281 as seen in FIG. 17 would normally be occupied by a therapy lead during use of the torque sleeve 280.

The clamp actuator 294 is configured to move the split ring 292 towards the proximal end 293 of the clamping section 295. In one or more embodiments, the clamp actuator 294 may be in the form of a wire attached to the split ring 292, with the wire extending proximally through the sleeve lumen 281 or a separate actuator lumen provided in the torque sleeve 280.

Figure 18:
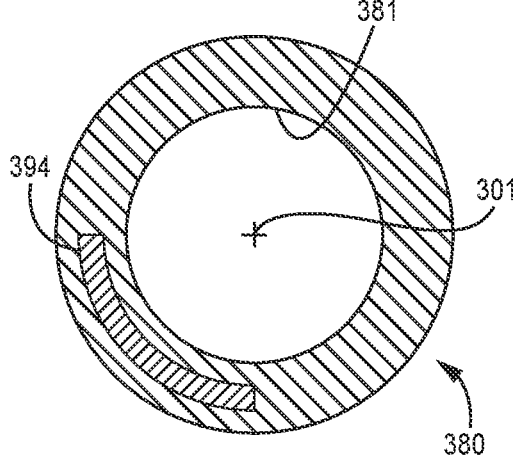
FIG. 18 it is a cross-sectional view of one alternative torque sleeve depicted in a cross-sectional view taken in a plane transverse to a catheter axis 301 depicting an alternative clamp actuator that may be used in one or more embodiments as described herein

Although the depicted embodiment of clamp actuator 294 is in the form of a wire, the clamp actuators used in clamp assemblies of torque sleeves as described herein may take any suitable form or shape that is capable of moving the split ring between the clamped and unclamped states as described herein. One example of an alternative clamp actuator is depicted in FIG. 18 where a cross-sectional view of torque sleeve 380 extending along catheter axis 301 is depicted. Similar to torque sleeve 280 as depicted in FIG. 17, torque sleeve 380 includes a sleeve lumen 381 that would typically be occupied by a therapy lead as described herein. The alternative clamp actuator 394 is in the form of an arcuately shaped partial sleeve that moves within a cavity within torque sleeve 380 that is of a complementary shape. Many other alternatives to the wire form actuator 294 and arcuate shaped actuator 394 are also possible.

When the split ring 292 is at the proximal end 293 of the clamping section 295, the split ring 292 is large enough such that the outer surface of the therapy lead 240 is not frictionally engaged by the split ring 292. This corresponds to the unclamped state of the clamp assembly.

The therapy systems and leads described herein may be used to deliver therapy and/or monitor electrical activity in tissue (e.g., cardiac or other tissue) of a patient and/or include components to accomplish those functions as described in, e.g., one or more of U.S. Patent Publication No. US 2016/0339248 entitled EFFICIENT DELIVERY OF MULTI-SITE PACING and U.S. Patent Publication No. US 2019/0111270 A1 entitled BUNDLE BRANCH PACING DEVICES AND METHODS.

The components of the medical electrode kits described herein may be constructed of any suitable material or combination of materials including, but not limited to, metals, polymers, conductive polymers, composites, etc., and combinations of one or more thereof, provided that the selected materials are capable of performing the functions required of the component. For example, conductive components may be formed by one or more electrically conductive wires or other structures, for example, MP35N alloy known to those skilled in the art, in a coiled or cabled configuration, and insulative tubular components may be any suitable medical grade polymer, for example, polyurethane, silicone rubber, or a blend thereof. In one or more embodiments, the flexible leads may extend over a pre-specified length (e.g., about 10 centimeters (cm) to about 20 cm, or about 15 to 20 cm) from a proximal end at which the lead is attached to an implantable medical device to the distal end of the lead. In one or more embodiments, the leads may have a size that is less than about 7 French (FR) or less.

ILLUSTRATIVE EMBODIMENTS

While the present disclosure is not so limited, an appreciation of various aspects of the disclosure will be gained through a discussion of the specific illustrative embodiments provided below. Various modifications of the illustrative embodiments, as well as additional embodiments of the disclosure, will become apparent herein.

Embodiment A is a medical electrode kit comprising: a delivery catheter extending along a catheter axis from a proximal catheter end to a distal catheter end, the delivery catheter comprising a delivery lumen extending from a distal opening at the distal catheter end towards the proximal catheter end; a catheter fixation structure located at the distal catheter end, the catheter fixation structure configured to attach the distal catheter end to tissue; a first lead assembly located in the delivery catheter lumen, the first lead assembly comprising: a push tube comprising a tube lumen extending from a distal tube opening proximally towards a proximal tube end, the push tube located within the delivery lumen extending along the catheter axis, and a first lead comprising a first electrode positioned at the distal tube opening and a first conductor attached to the first electrode, the first conductor extending proximally away from the first electrode and towards the proximal tube end; and a second lead extending from a distal end to a proximal end along a second lead axis, the second lead comprising: a second lead body comprising a first lead lumen extending from a lead opening at the distal end of the second lead proximally towards the proximal end of the second lead, a lead fixation structure located at the distal end of the second lead, the lead fixation structure configured to attach the distal end of the second lead to tissue, and a second electrode exposed on an exterior surface of the second lead body, the second electrode located between the distal end of the second lead and the proximal end of the second lead, wherein the second electrode is configured to be spaced away from tissue to which the lead fixation structure is attached; wherein the second lead is configured for advancement over the first conductor of the first lead distally towards the first electrode after the push tube and the delivery catheter are both removed from the first conductor in a proximal direction, and wherein the first conductor is located in the first lead lumen when the second lead is advanced over the first conductor towards the first electrode.

Embodiment A2 is a kit according to Embodiment A, wherein the catheter fixation structure on the delivery catheter comprises a delivery catheter helix configured to advance into tissue when the delivery catheter is rotated about the catheter axis.

Embodiment A3 is a kit according to Embodiment A2, wherein the delivery catheter helix comprises a helically coiled wire.

Embodiment A4 is a kit according to any kit of Embodiment A, wherein the first electrode is configured for advancement into tissue upon application of a translational pushing force delivered along the catheter axis to the first lead using the push tube.

Embodiment A5 is a kit according to Embodiment A4, wherein the first electrode is configured to resist removal from tissue in a proximal direction along the first conductor.

Embodiment A6 it is a kit according to any of embodiments A4 to A5, wherein the first electrode comprises a tapered body comprising a base larger than a distal tip, wherein the first conductor is attached to the tapered body proximate the base.

Embodiment A7 is a kit according to any of Embodiments A to A6, wherein the first conductor extends proximally from the first electrode through the tube lumen of the push tube.

Embodiment A8 is a kit according to any of Embodiments A to A7, wherein the lead fixation structure comprises a second lead helix configured to advance into tissue when the second lead is rotated about the first conductor of the first lead.

Embodiment A9 is a kit according to Embodiment A8, wherein the second lead helix comprises a helically coiled wire.

Embodiment A10 is a kit according to any of Embodiments A to A9, wherein the kit further comprises: a torque sleeve comprising a sleeve lumen extending along a sleeve axis extending from a distal sleeve end to a proximal sleeve end, wherein the second lead is located in the sleeve lumen of the torque sleeve; and a clamp assembly located in a clamping section of the sleeve lumen proximate the distal sleeve end, wherein the clamp assembly is configured to couple the torque sleeve to the second lead when in a clamped state such that rotation of the torque sleeve about the first conductor causes corresponding rotation of the second lead, and wherein the clamp assembly is configured to decouple the torque sleeve from the second lead when the clamp assembly is in an unclamped state such that the torque sleeve is configured to be advanced over the second lead towards the distal end of the second lead.

Embodiment A11 is a kit according to Embodiment A10, wherein the clamp assembly prevents translational movement of the torque sleeve along the second lead body away from the first electrode when the clamp assembly is in the clamped state.

Embodiment A12 is a kit according to either one of Embodiment A10 or A11, wherein the clamping section of the sleeve lumen comprises a tapered diameter that increases when moving in the proximal direction away from the distal sleeve end, and wherein the clamp assembly comprises: a split ring configured to clamp an exterior surface of the medical lead when the split ring is located at a distal end of the clamping section, and a clamp actuator attached to the split ring, the clamp actuator extending proximally away from the split ring and towards the proximal sleeve end, wherein the clamp actuator is configured to move the split ring towards a proximal end of the clamping section, and further wherein the clamp assembly is in the unclamped state when the split ring is located at the proximal end of the clamping assembly.

Embodiment A13 is a kit according to Embodiment A12, wherein the clamp actuator is configured to move the split ring towards the distal sleeve end within the clamping section to move the clamping assembly from the unclamped state to the clamped state.

Embodiment A14 is a kit according to either one of Embodiment A12 or A13, wherein the clamp actuator comprises a wire attached to the split ring and extending proximally through the sleeve lumen away from the clamping section.

Embodiment B is a medical therapy system comprising an implantable medical device (IMD) configured to provide pacing of a patient's heart; and a medical electrode kit for according to any one of Embodiments A to A14, wherein the first lead and the second lead are configured to be connected to the IMD.

Embodiment C is an implanted medical therapy system comprising an implantable medical device (IMD) configured to provide pacing of a patient's heart, wherein the IMD is subcutaneously implanted in the patient; wherein the first lead and the second lead of a medical electrode kit according to any one of Embodiments A to A14 are implanted in the patient and connected to the IMD.

Embodiment C17 is an implanted medical therapy system according to Embodiment C, wherein the first lead and the second lead do not pierce or extend into the left ventricle.

Embodiment C18 is an implanted medical therapy system according to Embodiment C or Embodiment C17, wherein the first electrode of the first lead is positioned to stimulate the right bundle branch.

Embodiment C19 is an implanted medical therapy system according to either one of Embodiment C or Embodiment C17, wherein the first electrode of the first lead is positioned to stimulate the left bundle branch.

Embodiment C20 is an implanted medical therapy system according to any one of Embodiment C16 to Embodiment C19, wherein the second electrode of the second lead is located in the right ventricle.

Embodiment D is a method of implanting a medical electrode system comprising: advancing a distal catheter end of a delivery catheter into a right ventricle of a patient's heart; securing a catheter fixation structure at the distal catheter end of the delivery catheter at a selected location on the septal wall of the patient's heart after advancing the distal catheter end into the right ventricle; advancing a first lead assembly through a delivery lumen in the delivery catheter, wherein the first lead assembly comprises a push tube and a first lead comprising a first electrode and first conductor attached to the first electrode, wherein advancing the first lead assembly comprises pushing the first electrode out of the distal catheter end of the delivery catheter and into the septal wall to locate the first electrode in the septal wall, wherein the first conductor extends proximally from the first electrode into the delivery lumen of the delivery catheter after the first electrode is located in septal wall; removing the push tube from the first conductor of the first lead after the first electrode is located in septal wall; removing the catheter fixation structure of the delivery catheter from the septal wall after the first electrode is located in septal wall; removing the delivery catheter from the first conductor of the first lead after removing the catheter fixation structure of the delivery catheter from the septal wall; advancing a second lead over the first conductor of the first lead after removing the delivery catheter from the first conductor of the first lead, wherein at least a portion of the first conductor is located in a first lead lumen in a second lead body while advancing the second lead over the first conductor; and securing the second lead body to the septal wall by attaching a lead fixation structure at a distal end of the second lead to the septal wall after advancing a second lead over the first conductor of the first lead, wherein the second lead comprises a second electrode located in the right ventricle when the lead fixation structure of the second lead is attached to the septal wall.

Embodiment D22 is a method according to Embodiment D, the method further comprising delivering pacing energy to the first electrode after pushing the first electrode out of the distal catheter end of the delivery catheter and into the septal wall and monitoring the patient's heart to determine when the first electrode is located to effectively deliver electrical energy to a selected bundle branch in the septal wall.

Embodiment D23 is a method according to Embodiment D22, wherein the selected bundle branch is selected from the right bundle branch and the left bundle branch.

Embodiment D24 is a method according to any one of Embodiment D to Embodiment D23, wherein securing the catheter fixation structure of the delivery catheter at the selected location on the septal wall comprises rotating the delivery catheter and the catheter fixation structure about an axis located in the delivery catheter lumen.

Embodiment D25 is a method according to any one of Embodiment D to Embodiment D24, wherein attaching the lead fixation structure at the distal end of the second lead to the septal wall comprises rotating the lead fixation structure about the first conductor.

Embodiment D26 is a method according to any one of Embodiment D to Embodiment D25, wherein the second lead is located in a torque sleeve when the second lead is advanced over the first conductor of the first lead, the torque sleeve comprising a sleeve lumen extending along a sleeve axis extending from a distal sleeve end to a proximal sleeve end, wherein the distal sleeve end is located proximate the lead fixation structure at the distal end of the second lead; wherein securing the lead fixation structure at the distal end of the second lead to the septal wall comprises rotating the second lead about the first conductor using the torque sleeve while a clamp assembly located in a clamping section of the sleeve lumen proximate the distal sleeve end is in a clamped state in which the clamp assembly frictionally couples the torque sleeve to the second lead such that rotation of the torque sleeve about the first conductor causes corresponding rotation of the second lead; and wherein the method further comprises: decoupling the torque sleeve from the second lead after securing the lead fixation structure to the septal wall by moving the clamp assembly to an unclamped state in which the torque sleeve is able to move along the second lead; advancing the distal sleeve end over the second lead towards the septal wall after decoupling the torque sleeve from the second lead until the distal sleeve end contacts the septal wall; and moving the clamp assembly back to the clamped state in which the clamp assembly frictionally couples the torque sleeve to the second lead such that movement of the torque sleeve along the second lead is prevented.

Embodiment D27 is a method according to Embodiment D26, wherein the clamping section of the sleeve lumen comprises a tapered diameter that increases when moving in the proximal direction away from the distal sleeve end, and the clamp assembly comprises a split ring configured to clamp an exterior surface of the therapy lead when the split ring is located at a distal end of the clamping section, wherein the method comprises: moving the split ring towards a proximal end of the clamping section when the clamp assembly is in the clamped state moves the clamp assembly to the unclamped state; and moving the split ring towards the distal end of the clamping section, when the clamp assembly is in the unclamped state, moves the clamp assembly to the clamped state.

Embodiment D28 is a method according to Embodiment D27, wherein the clamp assembly comprises a clamp actuator attached to the split ring, the clamp actuator extending proximally away from the split ring and towards the proximal sleeve end, wherein moving the split ring towards the proximal end of the clamping section comprises moving the clamp actuator in the proximal direction within the torque sleeve, and wherein moving the split ring towards the distal end of the clamping section comprises moving the clamp actuator in the distal direction within the torque sleeve.

Embodiment D29 is a method according to Embodiment D28, wherein the clamp actuator comprises a wire attached to the split ring and extending proximally through the sleeve lumen away from the clamping section.

Embodiment D30 is a method according to any one of Embodiment D to Embodiment D25, wherein the second lead is located in a torque sleeve when the second lead is advanced over the first conductor of the first lead, the torque sleeve comprising a sleeve lumen extending along a sleeve axis extending from a distal sleeve end to a proximal sleeve end, wherein the distal sleeve end is located proximate the lead fixation structure at the distal end of the second lead; wherein securing the lead fixation structure at the distal end of the second lead to the septal wall comprises rotating the second lead about the first conductor using the torque sleeve while a clamp assembly located in a clamping section of the sleeve lumen proximate the distal sleeve end is in a clamped state in which the clamp assembly frictionally couples the torque sleeve to the second lead such that rotation of the torque sleeve about the first conductor causes corresponding rotation of the second lead; and wherein the method further comprises: decoupling the torque sleeve from the second lead after securing the lead fixation structure to the septal wall by moving the clamp assembly to an unclamped state in which the torque sleeve is able to move along the second lead; and retracting the torque sleeve from the second lead in the proximal direction.

Embodiment E is a catheter assembly comprising: a therapy lead extending along a catheter axis from a proximal lead end to a distal lead end, the therapy lead comprising one or more electrodes proximate the distal lead end; a lead fixation structure located at the distal lead end of the therapy lead, the catheter fixation structure configured to attach the distal lead end to tissue; a torque sleeve comprising a sleeve lumen extending along a sleeve axis extending from a distal sleeve end to a proximal sleeve end, wherein the therapy lead is located in the sleeve lumen of the torque sleeve; and a clamp assembly located in a clamping section of the sleeve lumen proximate the distal sleeve end, wherein the clamp assembly is configured to frictionally couple the torque sleeve to the therapy lead when in a clamped state such that rotation of the torque sleeve about the catheter axis causes corresponding rotation of the therapy lead, and wherein the clamp assembly is configured to decouple the torque sleeve from the therapy lead when the clamp assembly is in an unclamped state such that the torque sleeve is configured to be advanced over the therapy lead towards the distal lead end.

Embodiment E32 is a catheter assembly according to Embodiment E, wherein the clamp assembly prevents translational movement of the torque sleeve along the therapy lead away from the distal lead end when the clamp assembly is in the clamped state.

Embodiment E33 is a catheter assembly according to either one of Embodiment E or Embodiment E32, wherein the clamping section of the sleeve lumen comprises a tapered diameter that increases when moving in the proximal direction away from the distal sleeve end, and wherein the clamp assembly comprises: a split ring configured to clamp an exterior surface of the therapy lead when the split ring is located at a distal end of the clamping section, and a clamp actuator attached to the split ring, the clamp actuator extending proximally away from the split ring and towards the proximal sleeve end, wherein the clamp actuator is configured to move the split ring towards a proximal end of the clamping section, and further wherein the clamp assembly is in the unclamped state when the split ring is located at the proximal end of the clamping assembly.

Embodiment E34 is a catheter assembly according to Embodiment E33, wherein the clamp actuator is configured to move the split ring towards the distal sleeve end within the clamping section to move the clamping assembly from the unclamped state to the clamped state.

Embodiment E35 is a catheter assembly according to any one of Embodiment E33 to Embodiment E34, wherein the clamp actuator comprises a wire attached to the split ring and extending proximally through the sleeve lumen away from the clamping section.

Embodiment E36 is a catheter assembly according to any one of Embodiment E to Embodiment E35, wherein the lead fixation structure on the therapy lead comprises a therapy lead helix configured to advance into tissue when the therapy lead is rotated about the catheter axis.

Embodiment E37 is a kit according to Embodiment E36, wherein the therapy lead helix comprises a helically coiled wire.

Embodiment F is a method of implanting a therapy lead, the method comprising: advancing a distal lead end of a therapy lead to a selected location in a patient's heart, wherein the therapy lead extends along a catheter axis from a proximal lead end to a distal lead end, the therapy lead comprising one or more electrodes proximate the distal lead end, and wherein a portion of the therapy lead is located in a torque sleeve comprising a sleeve lumen extending along a sleeve axis extending from a distal sleeve end to a proximal sleeve end, wherein the distal sleeve end is located proximate the distal lead end; securing a lead fixation structure at the distal lead end of the therapy lead to tissue at a selected location in the patient's heart after advancing the distal lead end to the selected location, wherein the securing comprises rotating the therapy lead about the catheter axis using the torque sleeve while a clamp assembly located in a clamping section of the sleeve lumen proximate the distal sleeve end is in a clamped state in which the clamp assembly frictionally couples the torque sleeve to the therapy lead such that rotation of the torque sleeve about the catheter axis causes corresponding rotation of the therapy lead; decoupling the torque sleeve from the therapy lead after securing the catheter fixation structure to tissue at the selected location in the patient's heart by moving the clamp assembly to an unclamped state in which the torque sleeve is able to move along the therapy lead; advancing the distal sleeve end over the therapy lead towards the distal lead end after decoupling the torque sleeve from the therapy lead until the distal sleeve end contacts tissue surrounding the selected location; and moving the clamp assembly back to the clamped state in which the clamp assembly frictionally couples the torque sleeve to the therapy lead such that movement of the torque sleeve along the therapy lead is prevented.

Embodiment F39 is a method according to Embodiment F, wherein the clamping section of the sleeve lumen comprises a tapered diameter that increases when moving in the proximal direction away from the distal sleeve end, and the clamp assembly comprises a split ring configured to clamp an exterior surface of the therapy lead when the split ring is located at a distal end of the clamping section, wherein the method comprises: moving the split ring towards a proximal end of the clamping section when the clamp assembly is in the clamped state moves the clamp assembly to the unclamped state; and moving the split ring towards the distal end of the clamping section, when the clamp assembly is in the unclamped state, moves the clamp assembly to the clamped state.

Embodiment F40 is a method according to Embodiment F39, wherein the clamp assembly comprises a clamp actuator attached to the split ring, the clamp actuator extending proximally away from the split ring and towards the proximal sleeve end, wherein moving the split ring towards the proximal end of the clamping section comprises moving the clamp actuator in the proximal direction within the torque sleeve, and wherein moving the split ring towards the distal end of the clamping section comprises moving the clamp actuator in the distal direction within the torque sleeve.

Embodiment F41 is a method according to Embodiment F40, wherein the clamp actuator comprises a wire attached to the split ring and extending proximally through the sleeve lumen away from the clamping section.

Embodiment F42 is a method according to any one of Embodiment F to Embodiment F41, wherein the catheter fixation structure on the therapy lead comprises a therapy lead helix configured to advance into tissue when the therapy lead is rotated about the catheter axis.

Embodiment F43 is a method according to Embodiment F42, wherein the therapy lead helix comprises a helically coiled wire.

Embodiment F44 is a method according to any one of Embodiment F to Embodiment F43, wherein the selected location is the septal wall of the patient's heart.

Embodiment F45 is a method according to Embodiment F44, wherein the distal sleeve end is located in the right ventricle of the patient's heart.

All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all of the listed elements or a combination of at least two of the listed elements.

The phrases "at least one of," "comprises at least one of," and "one or more of" followed by a list refers to any one of the items in the list and any combination of two or more items in the list.

The invention claimed is:

1. A medical electrode kit comprising:
a delivery catheter extending along a catheter axis from a proximal catheter end to a distal catheter end, the delivery catheter comprising a delivery lumen extending from a distal opening at the distal catheter end towards the proximal catheter end;
a catheter fixation structure located at the distal catheter end, the catheter fixation structure configured to attach the distal catheter end to tissue;
a first lead assembly located in the delivery catheter lumen, the first lead assembly comprising:
a push tube comprising a tube lumen extending from a distal tube opening proximally towards a proximal tube end, the push tube located within the delivery lumen extending along the catheter axis, and
a first lead comprising a first electrode positioned at the distal tube opening and a first conductor attached to the first electrode, the first conductor extending proximally away from the first electrode and towards the proximal tube end; and
a second lead extending from a distal end to a proximal end along a second lead axis, the second lead comprising:
a second lead body comprising a first lead lumen extending from a lead opening at the distal end of the second lead proximally towards the proximal end of the second lead,
a lead fixation structure located at the distal end of the second lead, the lead fixation structure configured to attach the distal end of the second lead to tissue, and
a second electrode exposed on an exterior surface of the second lead body, the second electrode located between the distal end of the second lead and the proximal end of the second lead, wherein the second electrode is configured to be spaced away from tissue to which the lead fixation structure is attached;
wherein the second lead is configured for advancement over the first conductor of the first lead distally towards the first electrode after the push tube and the delivery catheter are both removed from the first conductor in a proximal direction, and wherein the first conductor is located in the first lead lumen when the second lead is advanced over the first conductor towards the first electrode.

2. A kit according to claim 1, wherein the catheter fixation structure on the delivery catheter comprises a delivery catheter helix configured to advance into tissue when the delivery catheter is rotated about the catheter axis.

3. A kit according to claim 2, wherein the delivery catheter helix comprises a helically coiled wire.

4. A kit according to claim 1, wherein the first electrode is configured for advancement into tissue upon application of a translational pushing force delivered along the catheter axis to the first lead using the push tube.

5. A kit according to claim 4, wherein the first electrode is configured to resist removal from tissue in a proximal direction along the first conductor.

6. A kit according to claim 1, wherein the first electrode comprises a tapered body comprising a base larger than a distal tip, wherein the first conductor is attached to the tapered body proximate the base.

7. A kit according to claim 1, wherein the first conductor extends proximally from the first electrode through the tube lumen of the push tube.

8. A kit according to claim 1, wherein the lead fixation structure comprises a second lead helix configured to advance into tissue when the second lead is rotated about the first conductor of the first lead.

9. A kit according to claim 8, wherein the second lead helix comprises a helically coiled wire.

10. A kit according to claim 1, wherein the kit further comprises:

a torque sleeve comprising a sleeve lumen extending along a sleeve axis extending from a distal sleeve end to a proximal sleeve end, wherein the second lead is located in the sleeve lumen of the torque sleeve; and a clamp assembly located in a clamping section of the sleeve lumen proximate the distal sleeve end, wherein the clamp assembly is configured to couple the torque sleeve to the second lead when in a clamped state such that rotation of the torque sleeve about the first conductor causes corresponding rotation of the second lead, and wherein the clamp assembly is configured to decouple the torque sleeve from the second lead when the clamp assembly is in an unclamped state such that the torque sleeve is configured to be advanced over the second lead towards the distal end of the second lead.

11. A kit according to claim 10, wherein the clamp assembly prevents translational movement of the torque sleeve along the second lead body away from the first electrode when the clamp assembly is in the clamped state.

12. A kit according to claim 10, wherein the clamping section of the sleeve lumen comprises a tapered diameter that increases when moving in the proximal direction away from the distal sleeve end, and wherein the clamp assembly comprises:

a split ring configured to clamp an exterior surface of the medical lead when the split ring is located at a distal end of the clamping section, a clamp actuator attached to the split ring, the clamp actuator extending proximally away from the split ring and towards the proximal sleeve end, wherein the clamp actuator is configured to move the split ring towards a proximal end of the clamping section, and further wherein the clamp assembly is in the unclamped state when the split ring is located at the proximal end of the clamping assembly.

13. A kit according to claim 12, wherein the clamp actuator is configured to move the split ring towards the distal sleeve end within the clamping section to move the clamping assembly from the unclamped state to the clamped state.

14. A kit according to claim 12, wherein the clamp actuator comprises a wire attached to the split ring and extending proximally through the sleeve lumen away from the clamping section.

15. A medical therapy system comprising:

an implantable medical device (IMD) configured to provide pacing of a patient's heart; and a medical electrode kit for according to claim 1, wherein the first lead and the second lead are configured to be connected to the IMD.

16. An implanted medical therapy system comprising:

an implantable medical device (IMD) configured to provide pacing of a patient's heart, wherein the IMD is subcutaneously implanted in the patient; and wherein the first lead and the second lead of a medical electrode kit according to claim 1 are implanted in the patient and connected to the IMD.

17. An implanted medical therapy system according to claim 16, wherein the first lead and the second lead do not pierce or extend into the left ventricle.

18. An implanted medical therapy system according to claim 16, wherein the first electrode of the first lead is positioned to stimulate the right bundle branch.

19. An implanted medical therapy system according to claim 16, wherein the first electrode of the first lead is positioned to stimulate the left bundle branch.

20. An implanted medical therapy system according to claim 16, wherein the second electrode of the second lead is located in the right ventricle.

* * * * *